United States Patent [19]

Johnston

[11] 4,281,734

[45] Aug. 4, 1981

[54] MULTI-FUNCTION CONTROL SYSTEM

[76] Inventor: Gary D. Johnston, 1801 Arcineiga, Clovis, N. Mex. 88101

[21] Appl. No.: 89,194

[22] Filed: Oct. 29, 1979

[51] Int. Cl.$^3$ .......................... B62D 1/24; B62D 11/04
[52] U.S. Cl. ..................................... 180/167; 180/6.5; 180/DIG. 3; 250/221; 318/16
[58] Field of Search .................. 180/6.5, 167, DIG. 3; 318/16, 587; 250/201, 215, 221; 280/242 WC

[56] References Cited

U.S. PATENT DOCUMENTS

| | | | |
|---|---|---|---|
| 3,037,570 | 6/1962 | Olson | 180/6.5 |
| 3,106,371 | 10/1963 | Brannin et al. | 244/83 |
| 3,111,181 | 11/1963 | Yatich | 180/6.5 |
| 3,374,845 | 3/1968 | Selwyn | 180/6.5 |
| 3,654,477 | 4/1972 | Benjamin, Jr. | 250/221 |
| 3,737,685 | 6/1973 | Sharp, Jr. | 250/221 |
| 3,806,725 | 4/1974 | Leitz | 250/201 |
| 4,078,627 | 3/1978 | Brown et al. | 180/6.5 |
| 4,207,959 | 6/1980 | Youdin et al. | 180/6.5 |

Primary Examiner—Joseph F. Peters, Jr.
Assistant Examiner—Donn McGiehan
Attorney, Agent, or Firm—Kanz & Timmons

[57] ABSTRACT

A multi-function control system for generating control signals in response to the movement of an operator's body is disclosed.

An arrangement of the multi-function control system for controlling the speed and direction of a wheelchair (12) includes a mirror (16) for mounting on the head of the operator, a housing (20) attached to the wheelchair, a light source (26) within the housing for shining on the mirror, light sensors (30, 32, 34, and 36) for sensing the light reflected by the mirror, and a control circuit (38) for driving the wheelchair motors (70 and 72) in response to the output signals of the light sensors. The housing forms an opening facing toward the mirror when the operator's head is in the normal forward position.

The control circuit includes an input (39) that responds to the output signals of the light sensors, a signal processing circuit (43), and an output (53) which responds to the signal processing circuit.

The multi-function control system allows the operator to control the speed and direction of the wheelchair using only slight head movements without bulky equipment being connected to the operator and without electrical connections between apparatus carried on the operator's body and the wheelchair.

2 Claims, 9 Drawing Figures

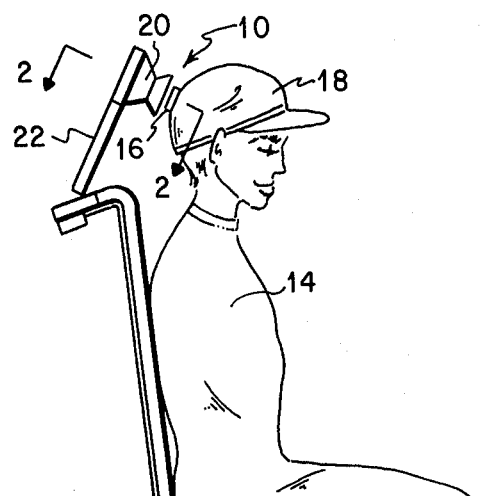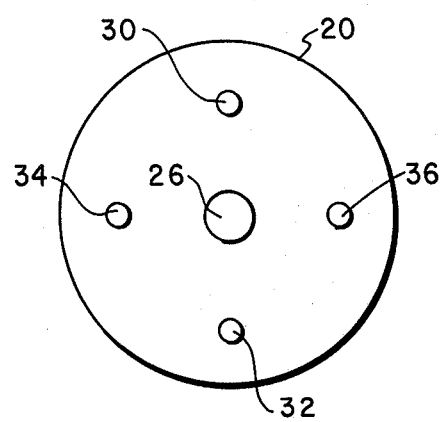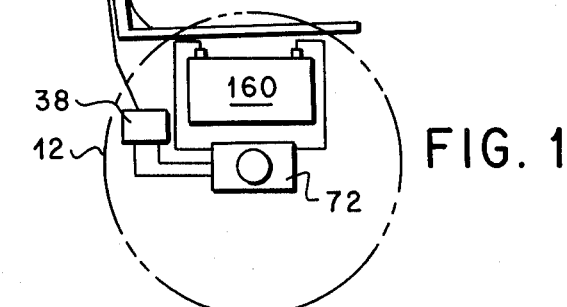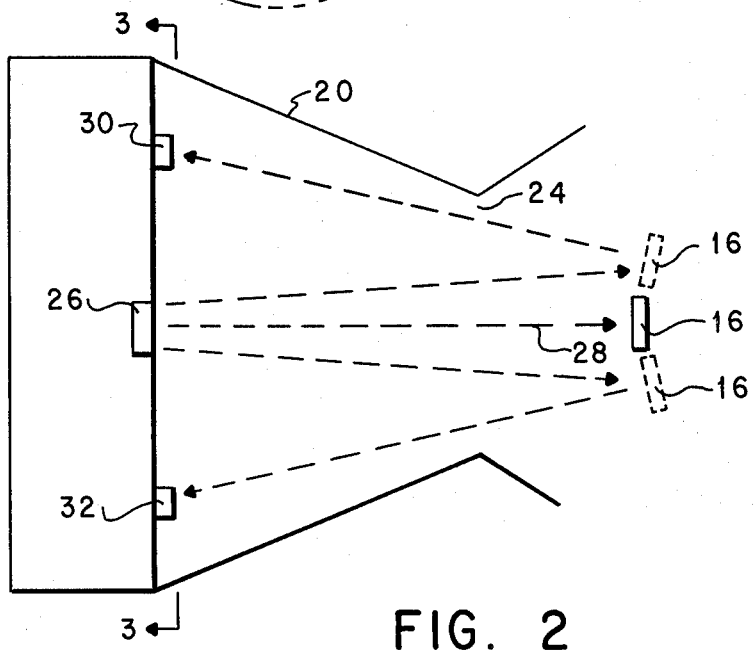
FIG. 1
FIG. 2
FIG. 3

MULTI-FUNCTION CONTROL SYSTEM

TECHINCAL FIELD

The present invention relates generally to multi-function control systems, and in one of its aspects, to a control system for a wheelchair.

In many situations, the operator of a vehicle will not have free use of his hands for operating the vehicle. Such restrictions may be due to the necessity of performing other functions with the hands as in farming or industrial operations or due to environmemtal influences such as excessive acceleration forces in aircraft. Quadriplegics also suffer from restricted use of the hands or feet in determining the speed and direction of motorized wheelchairs. A quadriplegic suffers especially from the inability to determine the speed and direction of his wheelchair since the limitation is of a continuing nature, making the individual completely dependent on others for traveling even small distances.

BACKGROUND ART

U.S. Pat. No. 3,374,845 issued to Selwyn shows a wheelchair control system in which the wheelchair is controlled by the movement of the operator's head. A housing structure is attached to the operator's body, in particular, a housing structure in the form of a helmet is worn on the operator's head. A sensing assembly is carried by the housing structure and is connected by wires to logic circuitry located on the wheelchair. The sensing assembly shown includes gravity actuated switches. The control system shown requires the operator to wear a helmet having equipment located within the helmet. It also requires some form of electrical connection from the equipment in the helmet to the control system circuitry on the wheelchair. It involves the inconvenience of physically connecting the operator to the wheelchair by means of the electrical connections, and also necessitates the use of a bulky and unsightly helmet on the operator's head. The helmet also adds a certain amount of weight on the head of the operator who probably has restricted neck strength.

DISCLOSURE OF INVENTION

In accordance with the present invention, a multi-function control system generates a plurality of distinct control signals in response to the components of movement of an operator's body with respect to a means for accommodating the operator. The multi-function control system includes a mirror, means for attaching the mirror to the operator's body, a housing, and means for attaching the housing to the means for accommodating the operator. The housing forms an opening facing toward the mirror when the operator's body is in a preselected position. The control system also includes a light source and means for attaching the light source to the means for accommodating the operator. The light source shines on the mirror when the operator's body is in the preselected position. Means for sensing the light reflected by the mirror is carried by the housing structure for responding to the different components of movement of the mirror and providing output command signals operatively related to the particular directional components of movement of the mirror. A control circuit includes an input which is responsive to the output signals of the light sensing means, means responsive to the input for processing signals, and an output responsive to the means for processing signals.

In one arrangement, the light source is attached within the housing for shinning substantially perpendicular to the mirror when the operator's body is in the preselected position.

In a preferred arrangement, the means for sensing the light reflected by the mirror includes at least three light sensors which are substantially equally spaced around the light source and substantially equal distances from the light source.

In an arrangement especially adapted for a wheelchair or other vehicle, a mirror is mounted on the head of the operator, and a housing is attached to the vehicle. The housing forms an opening facing toward the mirror when the head of the operator is in the normal forward position. A light source within the housing shines substantially perpendicular to the mirror when the head of the driver is in the normal forward position. Means within the housing for sensing the light reflected by the mirror responds to the different components of movement of the mirror and provides command signals operatively related to the particular directional components of the movement of the mirror. A control circuit includes an input responsive to the output signals of the light sensing means, means responsive to the input for processing signals, and an output responsive to the means for processing signals.

One embodiment of the means for sensing the light reflected by the mirror includes two turn control light sensors and two direction control light sensors. One turn control light sensor is spaced apart from the light source to the operator's right and the other sensor is spaced apart from the light source to the operator's left. One direction control sensor is spaced apart from the light source in the direction of forward rotation of the operator's head, and the other direction control sensor is spaced apart from the light source in the direction of backward rotation of the operator's head. Separate motors drive the right and left sides of the vehicle, having both forward and reverse drives. The motor for driving the right side of the vehicle has a forward drive which is responsive to the left turn control light sensor and one of the direction control light sensors and a reverse drive which is responsive to the right turn control light sensor and the other direction control light sensor. The motor for driving the left side of the vehicle has a forward drive responsive to the right turn control light sensor and the first direction control light sensor and a reverse drive responsive to the left turn control light sensor and the other direction control light sensor.

These and other objects, advantages and features of this invention will apparent from the following description taken with reference to the accompanying drawings, wherein is shown the preferred embodiments of the invention.

BRIEF DESCRIPTION OF DRAWINGS

FIG. 1 is a pictorial representation of an apparatus according to the present invention in use by an operator for controlling the direction and speed of a vehicle;

FIG. 2 is a sectional view of a housing of this invention taken at 2—2 of FIG. 1;

FIG. 3 is a sectional view taken at 3—3 of FIG. 2;

BEST MODE FOR CARRYING OUT THE INVENTION

Figure 4:
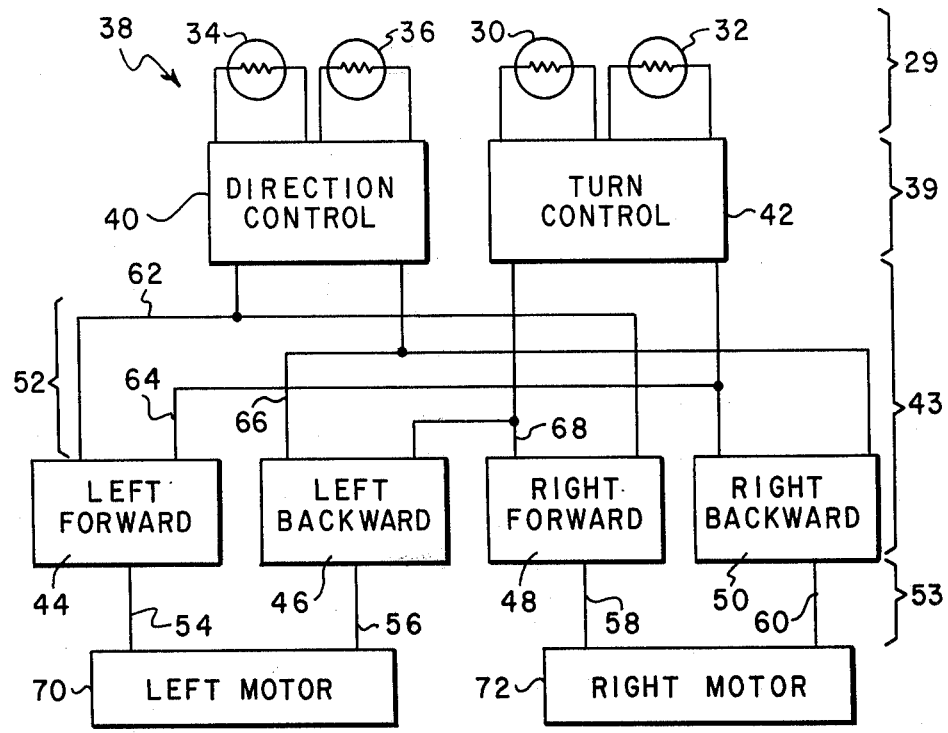
FIG. 4 is a block diagram of one arrangement of an apparatus according to the present invention for controlling the direction and speed of a vehicle.

Referring now to the drawings, and in particular to FIG. 1, an apparatus according to the present invention for controlling the direction and speed of a vehicle is referred to generally by reference numeral 10. Apparatus 10 is for controlling the direction and speed of a wheelchair 12 in response to head movements of an operator 14. A mirror 16 is mounted on the head 18 of operator 14. A housing 20 is attached to vehicle 12 by means 22.

Referring also to FIG. 2, housing 20 forms an opening 24 facing toward mirror 16 when head 18 of operator 14 is in the normal forward position. A light source 26 within housing 20 shines substantially perpendicular to mirror 16 when the head of the operator is in the normal forward position, as shown pictorially by dashed line 28. When the operator's head faces to the right, the back of his head and mirror 16 move to the left as shown by dashed position 16a. Similarly, when the operator's head faces to the left, the back of his head and mirror 16 move to the right as shown by dashed position 16b.

Referring to FIG. 3, two turn control light sensors 30 and 32, and first and second direction control light sensors 34 and 36 act together to form one means within housing 20 for sensing the light reflected by mirror 16, corresponding to the different components of movement of the mirror, and providing command signals operatively related to the particular directional components of movement of the mirror. One of the turn control light sensors 32 is spaced apart from light source 26 to the operator's right and the other sensor is spaced apart from the light source to the operator's left. First direction control light sensor 34 is spaced apart from light source 26 in the direction of forward rotation of the operator's head, and the other direction control light sensor, second direction control light sensor 36, is spaced apart from light source 26 in the direction of backward rotation of the operator's head. When mirror 16 is in position 16a, then it reflects more light toward light sensor 30 than it does toward light sensor 32. Likewise, when mirror 16 is in position 16b, then it reflects more light toward light sensor 32 than it does toward light sensor 30. The components of movement of the operator's head similarly control the amount of light reflected toward direction control light sensors 34 and 36.

Referring again to FIG. 1, and also to FIG. 4, a control circuit 38 includes an input 39 responsive to the output signals of light sensing means 29, means 43 responsive to input 39 for processing signals, and an output 53 responsive to means 43 for processing signals. The output signals of control circuit 38 provide the signals for controlling the direction and speed of the vehicle, wheelchair 12. Input 39 includes direction control 40 which is responsive to direction control light sensors 34 and 36, and turn control 42 which is responsive to turn control light sensors 30 and 32. Means 43 for processing signals includes a left forward control 44, a left backward control 46, a right forward control 48, and a right backward control 50 in addition to interconnections 52 between input 39 and the specific controls. Left forward control 44 is responsive to a forward output 62 from direction control 40 and a left turn output 64 from turn control 42. Left backward control 46 is responsive to a backward output 66 from direction control 40 and a right turn output 68 of turn control 42. Similarly, right forward control 48 is responsive to forward output 62 of direction control 40 and right turn output 68 of turn control 42, and right backward control 50 is responsive to backward output 66 of direction control 40 and left turn output 64 of turn control 42.

Left motor 70 and right motor 72 independently drive the left wheel and right wheel respectively of wheelchair 12. A preferred manner of turning wheelchair 12 to the right without moving it significantly forward or backward is to drive right motor 72 backward and left motor 70 forward. To move wheelchair 12 forward, both left motor 70 and right motor 72 should be driven forward. Similarly, to move wheelchair 12 backward, left motor 70 and right motor 72 are driven backwards. To turn wheelchair 12 to the left without moving it forward or backward, left motor 70 is driven backward and right motor 72 is driven forward. Left motor 70 has two windings, a forward winding driven by left forward control 44 through lead 54 and a backward winding driven by left backward control 46 through lead 56. Similarly, right motor 72 has two windings, a forward winding driven by right forward control 48 through lead 58 and a backward winding driven by right backward control 50 through lead 60. It can thus be seen, that right motor 72 for driving the right side of wheelchair 12 has a forward drive responsive through control circuit 38 to left turn control light sensor 32 which is on the operator's right and first direction control light sensor 34. The reverse drive is responsive through control circuit 38 to right turn control light sensor 30 which is on the operator's left and second direction control light sensor 36. In a similar manner, motor 70 for driving the left side of wheelchair 12 has a forward drive responsive through control circuit 38 to right turn control light sensor 30 and first direction control light sensor 34. Left motor 70 also has a reverse drive responsive through control circuit 38 to left turn control light sensor 32 and second direction control light sensor 36.

Figure 5:
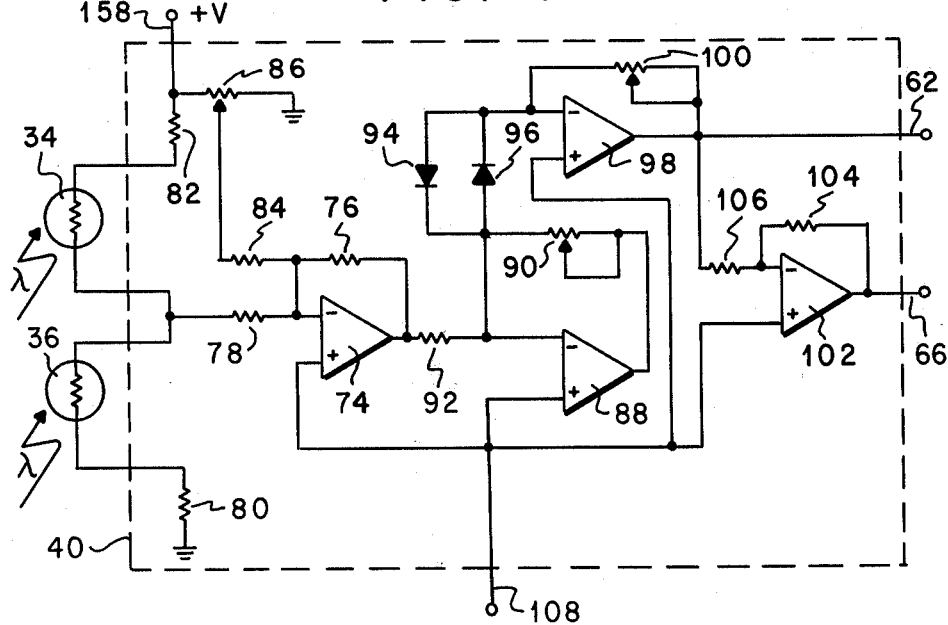
FIG. 5 is an electrical schematic diagram of the directional control of FIG. 4.

Referring now to FIG. 5, direction input circuit 40 includes an input stage made up of operational amplifier 74, feedback resistor 76, input resistor 78 and a balancing network made up of resistors 80, 82, 84, and potentiometer 86. Typically, potentiometer 86 is a 10K ohm potentiometer, and resistors 76, 78, and 84 are 100K ohms each. Potentiometer 86 along with resistors 80, 82, and 84 are used to balance the inputs from direction control light sensors 34 and 36 so that wheelchair 12 moves neither forward nor backward when the head of operator 14 is in the normal position. A circuit "dead zone" is used much like the play in a steering wheel and includes operational amplifier 88, feedback potentiometer 90, input resistor 92, and oppositely biased diodes 94 and 96. Typically, feedback potentiometer 90 is a 10K ohm potentiometer and input resistor 92 is a 1K ohm resistor. The negative input to operational amplifier 88 is used as a stable reference voltage, and oppositely biased diodes 94 and 96 provide the necessary voltage drop in either direction before the input to the next stage to create the dead zone. The next stage, made up of operational amplifier 98 and feedback potentiometer 100 is used to adjust the maximum turn-on limit of the circuit. The maximum turn-on limit is the limit at which further head movement causes no further increase in the maximum power to be delivered to the motors. The limit of movement can be exceeded but the maximum power to the motors will not be changed. Typically, potentiometer 100 is a 10K ohm potentiometer. Operational amplifier 102 along with its feedback resistor 104 and input resistor 106 merely inverts the output on forward output 62. Typically, feedback resistor 104 and input resistor 106 are 10K ohms each. The positive input to each of the operational amplifiers is connected to a reference voltage 108.

Figure 6:
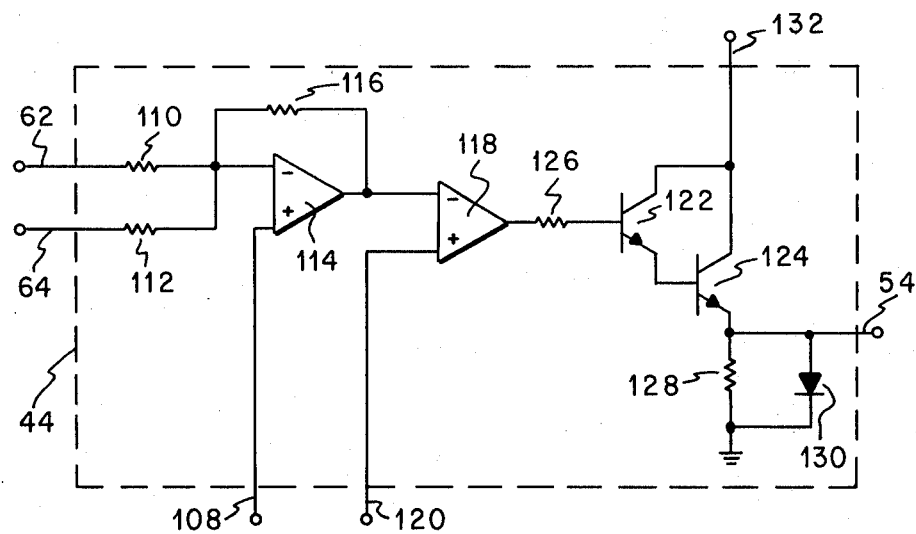
FIG. 6 is an electrical schematic diagram of the left forward drive of the apparatus of FIG. 4.

Referring now to FIG. 6, input resistors 110 and 112 from forward output line 62 and left turn output line 54 respectively are connected to the negative input of operational amplifier 114 which sums the inputs. The positive input of operational amplifier 114 is connected to reference voltage 108, and the summing stage uses feedback resistor 116, a typical value being 10K ohms. Operational amplifier 118 provides pulse width modulation of the summed inputs to operational amplifier 114 by comparing those summed inputs at its negative input to a triangular wave at its positive input 120. Assuming a 12 volt dc battery for a power supply, a typical triangular wave voltage input for positive input 120 would vary between 6 volts and 10 volts. The pulse width modulated output of operational amplifier 118 is followed by a beta multiplier composed of transistors 122 and 124 along with input resistor 126 and an emitter resistor 128 in parallel with diode 130. The beta multiplier is powered directly from the 12 volt battery at collector node 132. Output 54 is a pulse width modulated output for driving left motor 70 forward. The other control drives 46, 48, and 50 work in a similar manner. The pulse frequency is constant when the circuit is running, and to increase power to the motors, the pulses are lenghtened. To decrease power to the motors, the pulses are made shorter. This allows the motors to run cooler at any speed since they receive the full 12 volts for the duration of the pulses. It also enables the control to be linear so that operator 14 can go any speed from the minimum speed to the maximum speed in either direction or from a slight turn to a maximum turn in either direction. If movement of the head is in the dead zone for both forward and reverse as well as left and right, then no pulses are sent to the motors.

Figure 7:
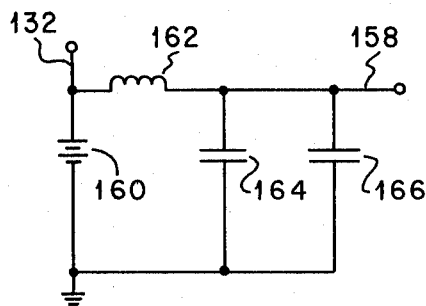
FIG. 7 is an electrical schematic diagram of one circuit for generating a reference voltage for the apparatus of the present invention.

Referring now to FIG. 7, reference voltage 108 is generated by a tight feedback loop on operational amplifier 134 with positive input to amplifier 134 determined by a voltage divider between resistor 136 and resistor 138. Capacitor 140 between the ouput of operational amplifier 134 and ground serves to further filter the output.

Figure 8:
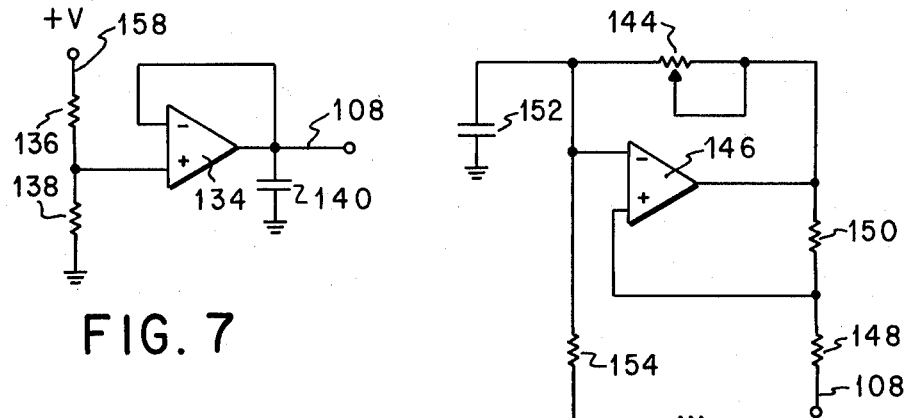
FIG. 8 is an electrical schematic diagram of one circuit for generating a triangular voltage wave for one arrangement of an apparatus according to the present invention.

Referring to FIG. 8, the triangular voltage wave is generated at line 120 which is the output of operational amplifier 142. Potentiometer 144 is used to adjust the frequency of a triangler wave generator which includes operational amplifier 146, input resistor 148 connected to the positive input of operational amplifier 146, positive feedback resistor 150, and capacitor 152 connected between the negative input of operational amplifier 146 and ground. Resistor divider made up of resistor 154 and resistor 156 is also connected between the negative input and ground.

Figure 9:
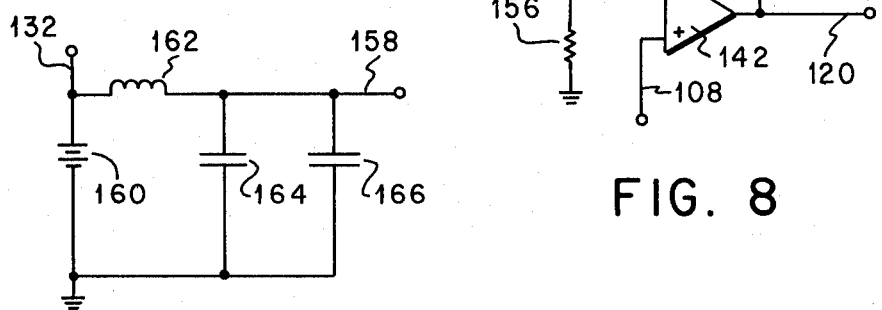
FIG. 9 is an electrical schematic diagram of a power source for the present invention.

Referring now to FIG. 9, a filtered dc source voltage 158 is used for supplying power to the operational amplifiers. Voltage 158 is provided from 12 volt battery 160 through the low pass LC filter made up of inductance coil 162 and capacitors 164 and 166.

In more general terms, the present invention is a multi-function control system for generating a plurality of distinct control signals responsive to the components of movement of an operator's body with respect to a means for accommodating the operator, in the case illustrated, the wheelchair itself. The movement of the operator's body must be in selectively determined command directions such as the forward and backward movement of the operator's head or the left and right movement of the operator's head. The control circuit output signals provide the plurality of distinct control signals. In the specific embodiment shown, the distinct control signals are supplied to motors, but they could also be for other purposes. A means for sensing the light reflected by the mirror using four light sensors is shown, but a system using three light sensors substantially equally spaced around the light source and substantially equal distances from the light source will work and have some advantages such as using fewer elements and having a reduced chance for conflicting signals.

From the foregoing it will be seen that this invention is one well adapted to attain all of the ends and objects hereinabove set forth, together with other advantages which are obvious and which are inherent to the apparatus. It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

I claim:

1. An apparatus for controlling the direction and speed of a vehicle in response to head movements of an operator, comprising in combination;

a mirror for mounting on the head of the operator;
   a housing;
   means for atttaching the housing to the vehicle, the housing forming an opening facing toward the mirror when the head of the operator is in the normal forward position;
   a light source within the housing for shining substantially perpendicular to the mirror when the head of the operator is in the normal forward position;
   means within the housing for sensing the light reflected by the mirror, for responding to the different components of movement of the mirror, and providing command signals operatively related to the particular directional components of movement of the mirror; and
   a control circuit including an input responsive to the output signals of the light sensing means, means responsive to the input for processing signals, and an output responsive to the means for processing signals;

wherein the control circuit output signals provide the signals for controlling the direction and speed of the vehicle.

2. An apparatus according to claim 1 wherein the means for sensing the light reflected by the mirror comprises, in combination:

two turn control light sensors, one sensor spaced apart from the light source to the operator's right and the other sensor spaced apart from the light source to the operator's left; and first and second direction control light sensors, one direction control light sensor spaced apart from the light source in the direction of forward rotation of the operator's head and the other direction control light sensor spaced apart from the light source in the direction of backward rotation of the operator's head; and wherein the apparatus further comprises, in combination:

a motor for driving the right side of the vehicle, having a forward drive responsive through the control circuit to the left turn control light sensor and the first direction control light sensor and a reverse drive responsive through the control circuit to the right turn control light sensor and the second direction control light sensor; and a motor for driving the left side of the vehicle, having a forward drive responsive through the control circuit to the right turn control light sensor and the first direction control light sensor and a reverse drive responsive through the control circuit to the left turn control light sensor and the second direction control light sensor.

* * * * *